(12) United States Patent
Chandler et al.

(10) Patent No.: US 8,693,004 B2
(45) Date of Patent: Apr. 8, 2014

(54) DUAL-ETALON CAVITY RING-DOWN FREQUENCY-COMB SPECTROSCOPY WITH BROAD BAND LIGHT SOURCE

(75) Inventors: David W. Chandler, Livermore, CA (US); Kevin E. Strecker, Oakland, CA (US)

(73) Assignee: Sandia Corporation, Albuquerque, NM (US)

( * ) Notice: Subject to any disclaimer, the term of this patent is extended or adjusted under 35 U.S.C. 154(b) by 595 days.

(21) Appl. No.: 13/050,430

(22) Filed: Mar. 17, 2011

(65) Prior Publication Data

US 2012/0002212 A1  Jan. 5, 2012

Related U.S. Application Data

(60) Provisional application No. 61/360,949, filed on Jul. 2, 2010.

(51) Int. Cl.
*G01B 9/02* (2006.01)

(52) U.S. Cl.
USPC ............................. 356/454; 356/497; 356/484

(58) Field of Classification Search
USPC .................. 356/454, 484, 519, 497, 506, 479
See application file for complete search history.

(56) References Cited

U.S. PATENT DOCUMENTS

| | | | | |
|---|---|---|---|---|
| 3,915,573 A | * | 10/1975 | Knoll et al. | 356/454 |
| 4,941,747 A | * | 7/1990 | Dakin | 356/454 |
| 7,359,066 B2 | * | 4/2008 | Cummings et al. | 356/519 |
| 7,483,143 B2 | | 1/2009 | Sanders et al. | |

OTHER PUBLICATIONS

Alder, et al.—"Cavity-Enhanced Direct Frequency Comb Spectroscopy: Technology and Applications"—In Annual Review of Analytical Chemistry, vol. 3, pp. 175-205. Mar. 1, 2010.
Bernhardt et al.—"Cavity-enhanced dual-comb spectroscopy"—Nature Photonics, 4(1): 55-57, Jan. 10, 2010.
Cundiff et al.—"Optical frequency synthesis based on mode-locked lasers"—Review of Scientific Instruments, 72(1): 3749-3771, Oct. 2001.
Engeln et al.—"Polarization dependent cavity ring down spectroscopy"—In Frontiers in Low Temperature Plasma Diagnostics III. Book of Papers, pp. 39-49, Lausanne Switzerland, Feb. 1999. Centre de Recherches en Physique des Plasmas; Int. Union for Vacuum Sci. Tech. & Applications; Swiss Vacuum Soc.; et al., Ecole Polytechnique Federale de Lausanne. Proceedings of Workshop on Frontiers in Low Temperature Plasma Diagnostics III, Feb. 15-19, 1999, Saillon, Switzerland.
Engeln et al.—"Cavity enhanced absorption and cavity enhanced magnetic rotation spectroscopy"—Review of Scientific Instruments, vol. 69, No. 11, Nov. 1998.

(Continued)

*Primary Examiner* — Hwa Lee
(74) *Attorney, Agent, or Firm* — Marcus S. Simon

(57) ABSTRACT

In an embodiment, a dual-etalon cavity-ring-down frequency-comb spectrometer system is described. A broad band light source is split into two beams. One beam travels through a first etalon and a sample under test, while the other beam travels through a second etalon, and the two beams are recombined onto a single detector. If the free spectral ranges ("FSR") of the two etalons are not identical, the interference pattern at the detector will consist of a series of beat frequencies. By monitoring these beat frequencies, optical frequencies where light is absorbed may be determined.

21 Claims, 14 Drawing Sheets

(56) References Cited

OTHER PUBLICATIONS

Gohle et al. "Frequency comb cornier spectroscopy for broadband, high-resolution, high-sensitivity absorption and dispersion spectra"—Physical Review Letters, 99(26), Dec. 31, 2007.

Langridge et al.—"Cavity enhanced absorption spectroscopy of multiple trace gas species using a supercontinuum radiation source"—Optics Express, 16(14): 10178-10188, Jul. 7, 2008.

Morville et al.—"Two schemes for trace detection using cavity ringdown spectroscopy"—Applied Physics B-Lasers and Optics, 78(3-4):465-476, Feb. 2004.

Paldus et al.—"An historical overview of cavity-enhanced method"—Canadian Journal of Physics, 83(10): 975-999, Oct. 2005.

Sayres et al.—A new cavity based absorption instrument for detection of water isotopologues in the upper troposphere and lower stratosphere—Review of Scientific Instruments, 80(4): 044102 (14pp.), Apr. 2009.

Schiller—"Spectrometry with frequency combs"—Optics Letters, 27(9): 766-768, May 1, 2002.

Stelmaszczyk et al.—"Cavity Ring-Down Absorption Spectrography based on filament-generated supercontinuum light"—Optics Express, 17(5):3673-3678, Mar. 2, 2009.

Thorpe et al.—"Broadband cavity ringdown spectroscopy for sensitive and rapid molecular detection"—Science, 311(5767):1595-1599, Mar. 17, 2006.

Chandler et al.—"Dual-Etalon, Cavity-Ring-Down, Frequency Comb Spectroscopy"—Sandia National Laboratories, pp. 1-28, Oct. 2010.

Bernhardt et al.—"Cavity enhanced dual-comb spectroscopy"—*Nature Photonics*—vol. 4, pp. 55-57—Jan. 2010.

Newbury et al.—"Sensitivity of coherent dual-comb spectroscopy"—Optics Express—vol. 18, No. 8, pp. 7929-7945—Apr. 2010.

\* cited by examiner

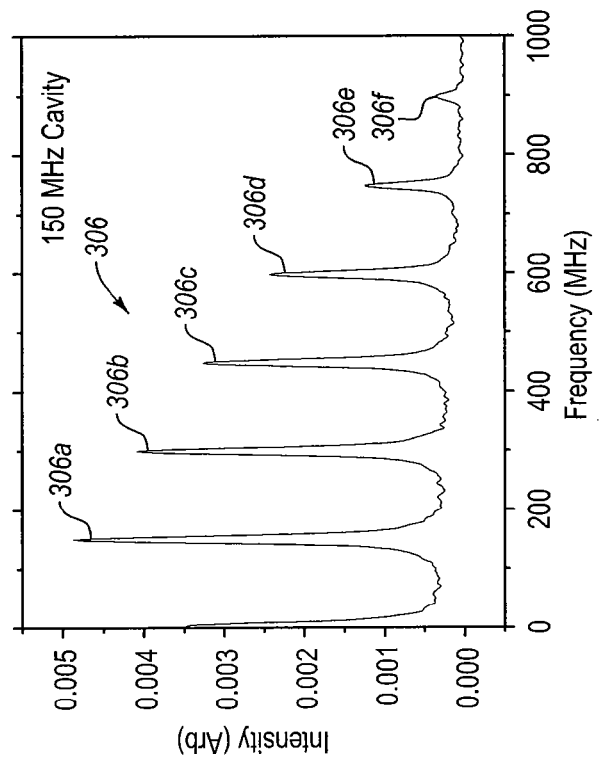
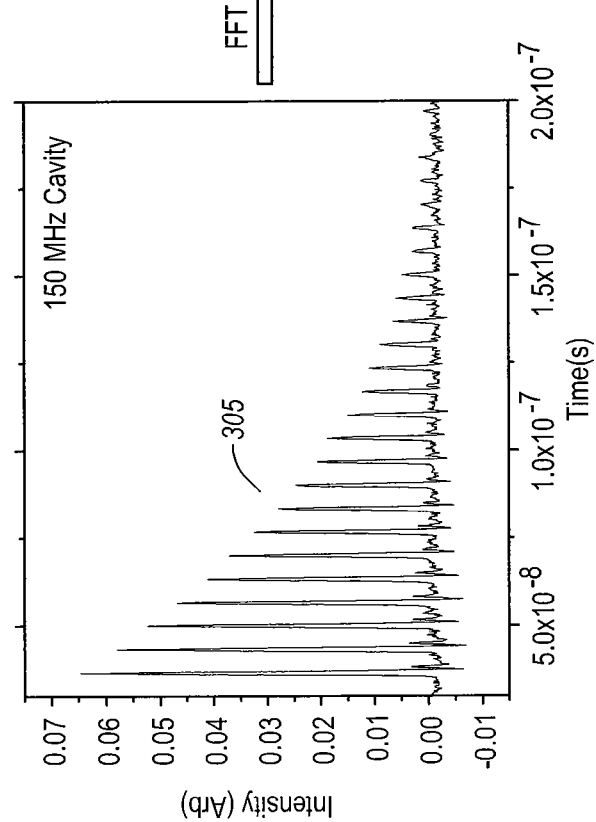
Fig. 3A
Fig. 3B

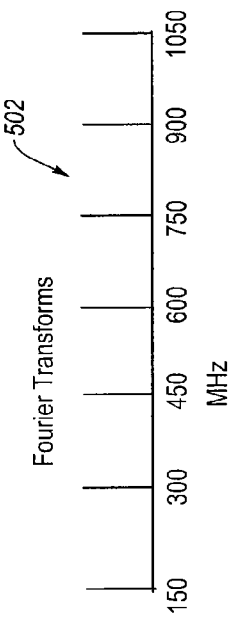
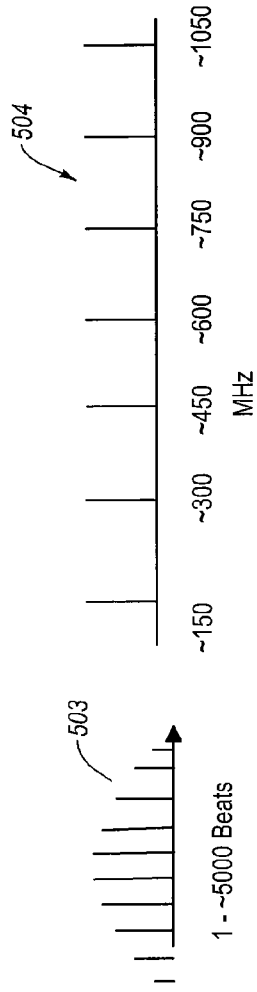
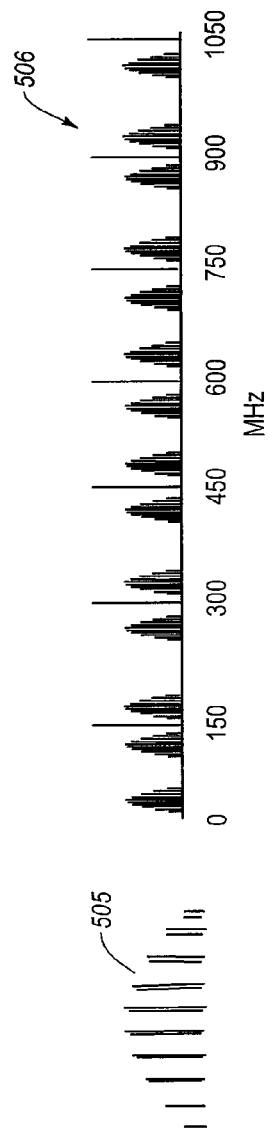
Fig. 5A
Fig. 5B
Fig. 5C

DUAL-ETALON CAVITY RING-DOWN FREQUENCY-COMB SPECTROSCOPY WITH BROAD BAND LIGHT SOURCE

CROSS-REFERENCE TO RELATED APPLICATIONS

This application claims the benefit of U.S. Provisional Patent Application Ser. No. 61/360,949, filed Jul. 2, 2010, which is incorporated herein by reference in its entirety.

STATEMENT REGARDING GOVERNMENT RESEARCH AND DEVELOPMENT

This invention was made with Government support under government contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

BACKGROUND

Absorption spectroscopy is one of the most quantitative methods for identifying unknown gases, liquids, and aerosols in either the laboratory or real world applications. For instance, in the infrared portion of the spectrum, many molecules contain a "fingerprint," a unique pattern of optical transitions that are distinct due to the compounds chemical moiety (OH, CH, CO). The primary issues with using absorption spectroscopy as an everyday tool for identifying environmental contaminates are that large spectral bandwidths with good resolution are needed and high sensitivity is required. Typically contaminates of the greatest concern/interest are very dilute in the environment so some manner of increasing the sensitivity of direct absorption methods are needed for sensor development.

Cavity-ring-down based spectrometers, which use optical resonators to increase the effective path length of the absorbing medium, are now routinely used to monitor green house gasses. However they are generally limited to measuring absorption at extremely narrow spectral regions associated with the laser light source used. Modern day state-of-the-art spectrometers attempt to overcome the issues of spectral resolution (selectivity) at the cost of bandwidth. Generally, high-resolution laser light sources are used that are resonant with an atomic or molecular transition of interest, but these sources are not broadly tunable. When using a broad light source the frequency resolution is limited by the spectrometer.

SUMMARY

Embodiments of the invention relate to systems for performing frequency-comb spectroscopy on a sample or other types of measurements. In an embodiment, a system includes at least one broad band light source that provides a light beam. The system also includes a first etalon. The first etalon may generate a first frequency-comb signal in response to receiving the light beam from the at least one broad band light source. The first frequency-comb signal defines a spectrum of light that includes multiple optical frequencies spaced by a first frequency spacing.

The system further includes a second etalon. The second etalon generates a second frequency-comb signal in response to receiving the light beam from the at least one broad band light source. The second frequency-comb signal defines a second spectrum of light that includes one or more optical frequencies spaced by a second frequency spacing that is different from the first frequency spacing. The system also includes a detector that detects multiple beat frequencies of the first and second frequency-comb signals.

Other embodiments disclosed herein relate to methods for performing frequency-comb spectroscopy on a sample. In an embodiment, a method includes generating at a first etalon a first frequency-comb signal in response to receiving a light beam. The first frequency-comb signal defines a spectrum of light that includes multiple optical frequencies spaced by a first frequency spacing.

The method also includes placing the sample before, inside, or outside of one or more of the first etalon or the second etalon such that the sample is in the path of the light beam received by the first etalon or both the first and second etalons. The method further includes generating at a second etalon a second frequency-comb signal in response to receiving the light beam. The second frequency-comb signal defines a second spectrum of light that includes one or more optical frequencies spaced by a second frequency spacing that is different from the first frequency spacing.

The method may further include detecting multiple beat frequencies of the first and second frequency-comb signals and analyzing the beat frequencies to determine optical frequencies absorbed by the sample.

These and other advantages and features of the present disclosure will become more fully apparent from the following description and appended claims, or may be learned by the practice of the embodiments as set forth hereinafter.

BRIEF DESCRIPTION OF THE DRAWINGS

To further clarify the advantages and features of the various embodiments of the invention, a more particular description will be rendered by reference to specific embodiments that are illustrated in the appended drawings. It is appreciated that these drawings depict only typical embodiments of the invention and are therefore not to be considered limiting of its scope. The various embodiments will be described and explained with additional specificity and detail through the use of the accompanying drawings in which:

FIGS. 3A-3D illustrate measured interference patterns and frequency spectrums for a first frequency-comb signal and a second frequency-comb signal;

FIGS. 5A-5C illustrate expected interference patterns and frequency spectrums for a first frequency-comb signal, a second frequency-comb signal, and a combined frequency-comb signal;

DETAILED DESCRIPTION

The embodiments disclosed herein describe dual-etalon cavity-ring-down frequency-comb spectrometer systems and other types of measurement systems that allow both high resolution and broad bandwidth measurements substantially simultaneously. In addition, the measurements require only a few microseconds and require no special light source or electronics.

The dual-etalon cavity-ring-down frequency-comb spectrometer systems rely upon a light beam from a bright broad bandwidth light source, such as a laser, a diode, or a lamp, that may be pulsed or continuous, which is split into two beams. One beam is directed through a first etalon having a free spectral range ("FSR") of the required spectroscopy. The first etalon creates a first frequency-comb signal. The light going to the first etalon is also directed through an absorbing medium. The absorbing medium may be positioned before, after or inside of the first etalon. If the absorbing medium is placed inside the first etalon, this is a cavity-ring-down arrangement and enhanced sensitivity is obtained.

The other light beam is directed through a second etalon and may or may not be subject to the absorbing medium. The second etalon creates a second frequency-comb signal that may either be a single frequency (obtained by using a short etalon with a large FSR) or multiple frequencies that are similar but not quite the same as the frequencies of the first frequency-comb signal coming from the absorption arm of the spectrometer. By combining the first and second frequency-comb signals on a photodiode and recording the resulting interference pattern obtained from beat frequencies of the first and second frequency-comb signals, an absorption frequency spectrum may be reconstituted. This absorption frequency spectrum will comprise a series of discrete absorption measurements with the spacing of the FSR of the first etalon each with the resolution associated with the convolution of the finesse of the first and second etalons.

In order to obtain 1 MHz resolution of the individual absorption measurements, a ring down time of the etalons of approximately 1 microsecond is typically required. If the interference pattern is analyzed in parts, every 100 nanoseconds for instance, then a time-resolved frequency spectrum with about 10 MHz spectral resolution and 100 nanoseconds time resolution may be obtained. In order to obtain 1 MHz spectral resolution with a traditional Michelson interferometer type of Fourier Transform spectrometer would require moving the mirror a kilometer distance. Additionally, in order to obtain the 100 nanosecond time-resolutions would require hours of operation in a step scan mode.

Figure 1A:
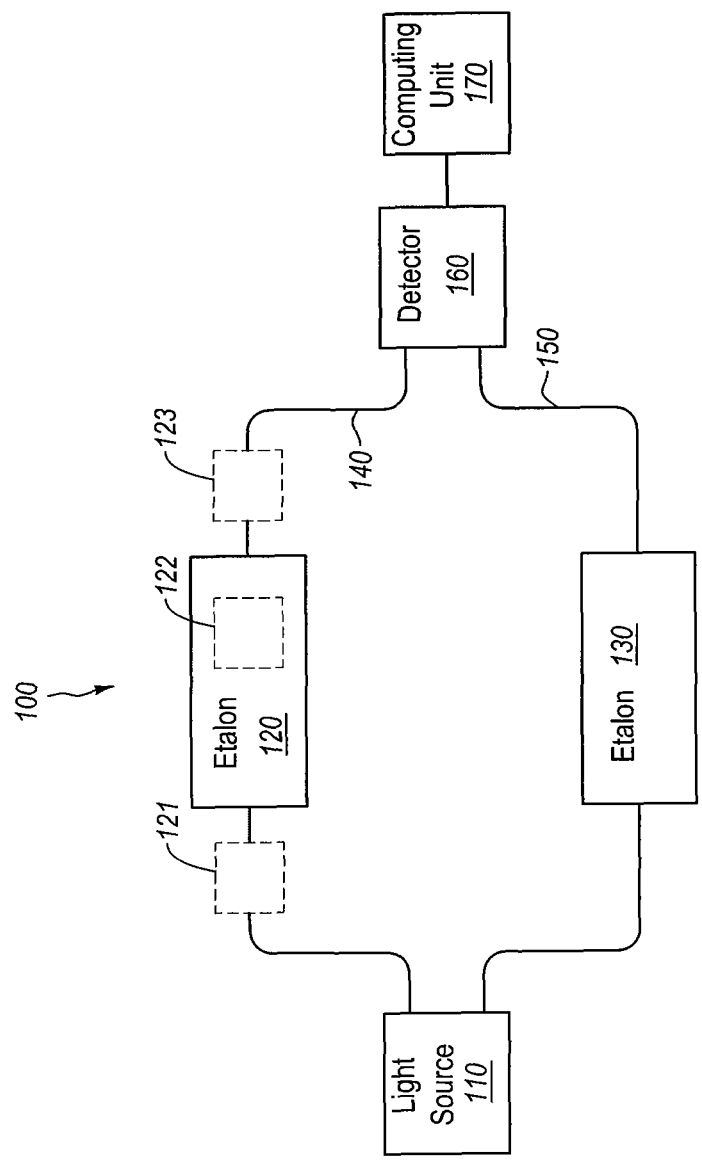
FIG. 1A illustrates an embodiment of a dual-etalon cavity-ring-down frequency-comb spectrometer system.

Embodiments of a Dual-Etalon Cavity-Ring-Down Frequency-Comb Spectrometer System Attention is now given to FIG. 1A, which illustrates a dual-etalon cavity-ring-down frequency-comb spectrometer system 100 according to an embodiment disclosed herein. The system 100 includes a broad band light source 110. The broad band light source 110 may provide a light beam to a first etalon 120 and a second etalon 130. The broad band light source 110 may be a non-frequency-comb laser or other non-frequency-comb light source. For example, the broad band light source 110 may be a pulsed laser, a continuous laser, an LED, a simple lamp, or other suitable light source. Thus, any non-frequency-comb light source may be used in the embodiments disclosed herein.

In one embodiment, the broad band light source 110 may be a Fourier transformed limited light pulse. Such a pulse may have a smooth intensity pattern of frequencies that allow one to read off the absorption from the resulting beat frequency pattern without the need for background subtraction data.

The system 100 also includes a first etalon 120 and a second etalon 130. In optics, an etalon (also referred to as a Fabry-Pérot interferometer) is typically made of a transparent plate with two reflecting surfaces, or two substantially parallel highly reflecting mirrors. A transmission spectrum of an etalon as a function of wavelength exhibits peaks of large transmission corresponding to resonances of the etalon. The varying transmission function of an etalon is caused by interference between the multiple reflections of light between the two reflecting surfaces. Constructive interference occurs if the transmitted beams are in phase, and this corresponds to a high-transmission peak of the etalon. If the transmitted beams are out-of-phase, destructive interference occurs and this corresponds to a transmission minimum. Whether the multiply-reflected beams are in-phase or not depends on the wavelength ($\lambda$) of the light (in vacuum), the angle the light travels through the etalon ($\theta$), the thickness of the etalon (l) and the refractive index of the material between the reflecting surfaces (n). Thus, a light beam is able to move multiple kilometers inside the etalon, while a location of the reflecting mirrors are maintained constant because the light beam reflects back and forth multiple times in the etalon.

In the dual-etalon cavity-ring-down frequency-comb spectrometer system 100, the first etalon 120 and the second etalon 130 are connected to the broad band light source 110 by any reasonable connection (e.g., fiber optic cables, other optical cables, reflective mirrors, or waveguides) and receive a light beam from the light source 110 over the reasonable connection. In one embodiment, as will be described in more detail to follow, the first etalon 120 may generate a first frequency-comb signal 140 in response to receiving the light beam from the light source 110. As will be explained, the first frequency-comb signal 140 may define a spectrum of light that includes multiple optical frequencies spaced by a first frequency spacing. In some embodiments, the first frequency spacing is determined by the FSR of the first etalon.

The first etalon 120 may be an absorption arm of the dual-etalon cavity-ring-down frequency-comb spectrometer system 100 and may be used to test the absorption of a sample as will be described in more detail to follow. In one embodiment, the sample may be placed before the etalon 120 as indicated by dashed box 121. In another embodiment, the sample may be placed after the etalon 120 as indicated by the dashed box 123. In still other embodiments, the sample may be placed inside the etalon 120 as indicated by the dashed box 122. When the sample is placed inside the etalon 120, ring-down spectroscopy may be performed. When the sample is placed either before or after the etalon 120 (i.e., in close proximity to the etalon 120), then direct single or multi-pass absorption may be performed.

The second etalon 130 may be a read-out arm of the dual-etalon cavity-ring-down frequency-comb spectrometer system 100. The second etalon 130 may generate a second frequency-comb signal 150 in response to receiving the light beam from the light source 110. As will be explained, the second frequency-comb signal 150 may define a spectrum of light that includes one or more optical frequencies spaced by a second frequency spacing. In some embodiments, the second frequency spacing is determined by the FSR of the second etalon. When the FSR of the second etalon 130 is different from the FSR of the first etalon 120, then the first frequency spacing and the second frequency spacing will be different. In some embodiments, the FSR of the second etalon 130 may be larger or smaller than the FSR of the first etalon 120. In other embodiments, the FSR of the second etalon 130 may be nearly the same as the FSR of the first etalon 120.

Accordingly, the second frequency-comb signal 150 may be either a single frequency (obtained by using a short second etalon 130 with a large FSR) or multiple frequencies that are similar to, but not quite the same, as the frequencies of the first frequency-comb signal 140 obtained by using a second etalon 130 with an FSR nearly the same as the FSR of the first etalon 120. As will also be explained in more detail to follow, the difference in the first frequency spacing and the second frequency spacing cause beat frequencies that may be used to determine the absorption of the sample under test. It will be appreciated that the mirror to be used and the cavity lengths of the first and second etalons 120 and 130 may be adjusted depending on needed resolution and the bandwidth of the light source 110.

In some embodiments, the sample may also be placed in the second etalon 130. Although not illustrated in the figures, in such embodiments the sample may be placed before, after, or inside of the second etalon 130. Placing the sample is both the first etalon 120 and the second etalon 130 may be useful in applications such as measuring a chemical species in the air.

The dual-etalon cavity-ring-down frequency-comb spectrometer system 100 may also include a detector 160, which in some embodiments may be a photodiode, a photomultiplier tube, an infrared detector, or array of photodiodes. The detector 160 may receive the first frequency-comb signal 140 from the first etalon 120 and the second frequency-comb signal 150 from the second etalon 130 by any reasonable connection such as fiber optic cables, other optical cables, reflective mirrors, or waveguides. The detector 160 may then combine the first and second frequency-comb signals 140 and 150 and may detect the multiple beat frequencies of the first frequency-comb signal 140 and the second frequency-comb signal 150. That is, the interference caused by the difference between the first frequency spacing of the first frequency-comb signal 140 and the second frequency spacing of the second frequency-comb signal 150 creates the beat frequencies. The detector 160 may detect the interference pattern of the beat frequencies.

The dual-etalon cavity-ring-down frequency-comb spectrometer system 100 may further include a computing unit 170, which in some embodiments may be an oscilloscope that is able to perform Fourier Transforms on signals. The computing unit 170 may also be any other type of processing device that is able to perform Fourier transforms on signals. The computing unit 170 may be connected to the detector 160 by any reasonable connection such as fiber optic cables, reflective mirrors, or waveguides. The computing unit 170 may be configured to analyze the beat frequencies detected by the detector 160. In some embodiments, as will be explained in more detail to follow, the computing unit 170 is configured to obtain and record the interference pattern of the beat frequencies obtained by the detector 160. That is, in operation, the computing unit 170 receives from the detector 160 current readings corresponding to the time-domain interference pattern of the beat frequencies. The computing unit 170 may then reconstitute an absorption frequency spectrum of the beat frequencies by performing a Fourier transform operation on the interference pattern. The reconstituted absorption frequency spectrum may then be used to determine which of the beat frequencies were at least partially absorbed by the sample. This determination may be done by comparing the reconstituted absorption frequency spectrum obtained with the sample with a frequency spectrum obtained without the sample.

Figure 1B:
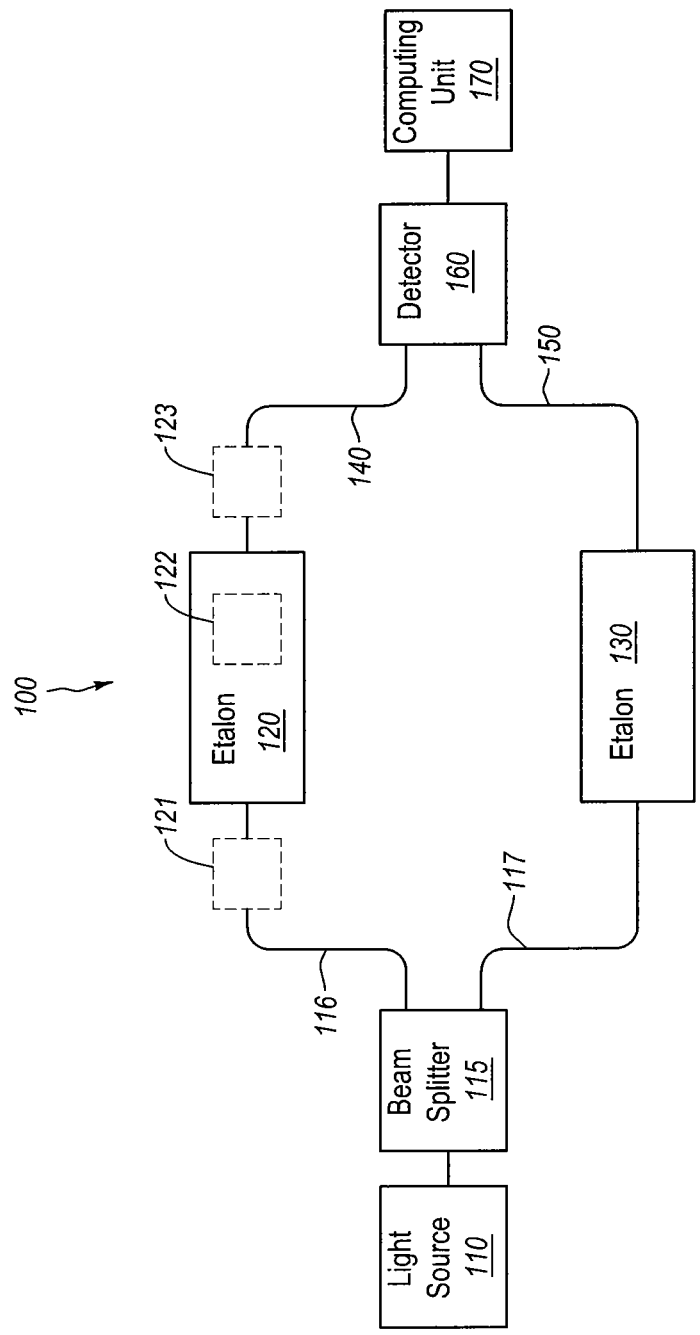
FIG. 1B illustrates another embodiment of a dual-etalon cavity-ring-down frequency-comb spectrometer system.

FIG. 1B illustrates another embodiment of the dual-etalon cavity-ring-down frequency-comb spectrometer system 100. The embodiment of FIG. 1B includes many of the same elements of the embodiment of FIG. 1A and such repeated elements will not be explained in relation to FIG. 1B. As illustrated, the dual-etalon cavity-ring-down frequency-comb spectrometer system 100 may include a beam splitter 115, which may be any suitable beam splitter. The beam splitter 115 may receive the light beam from the broad band light source 110 by any suitable connection such as fiber optic cables, or other, reflective mirrors, or waveguides. The beam splitter 115 may then split the light beam into a first portion 116 and a second portion 117. The first portion 116 may be provided to the first etalon 120 and the second portion 117 may be provided to the second etalon 130 by any suitable connection such as fiber optic cables, or other, reflective mirrors, or waveguides that connect the beam splitter 115 with the first and second etalons.

Figure 1C:
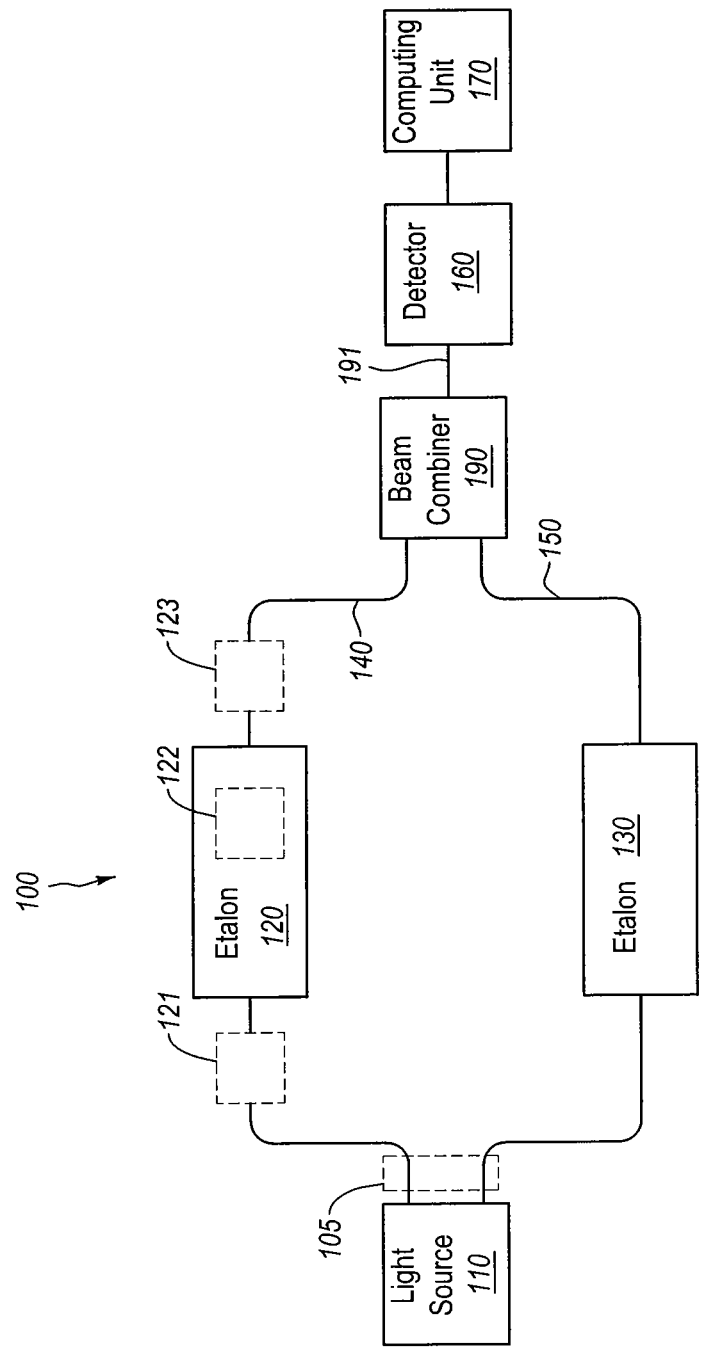
FIG. 1C illustrates another embodiment of a dual-etalon cavity-ring-down frequency-comb spectrometer system.

FIG. 1C illustrates yet another embodiment of the dual-etalon cavity-ring-down frequency-comb spectrometer system 100. The embodiment of FIG. 1C includes many of the same elements of the embodiment of FIG. 1A and such repeated elements will not be explained in relation to FIG. 1C. Although not illustrated, it will be appreciated that the embodiment of FIG. 1C may include the beam splitter 115 previously described. As illustrated, the dual-etalon cavity-ring-down frequency-comb spectrometer system 100 may include a beam combiner 190 connected to the first and second etalons 120 and 130 by any suitable connection, such as fiber optic cables, or other, reflective mirrors, or waveguides. The beam combiner 190 may receive the first frequency-comb signal 150 from the first etalon 120 and the second frequency-comb signal 150 from the second etalon 130 and may combine the two frequency-comb signals into a combined frequency-comb signal 191. The combined frequency-comb signal 191 may then be provided to the detector 160 for detection of the beat frequencies by any reasonable connection such as fiber optic cables, other optical cables, reflective mirrors, or waveguides that connect the beam combiner 190 with the detector 160.

FIG. 1C also shows an optical filter 105 that may be connected between the broad band light source 110 and the etalons 120 and 130. The optical filter 105 may be any suitable optical filter and is used to limit the bandwidth of the light beam from light source 110 before the light beam enters the etalons 120 and 130. The optical filter 105 may be utilized in those embodiments where the etalon 120 and/or 130 require a bandwidth limited light beam.

Figure 1D:
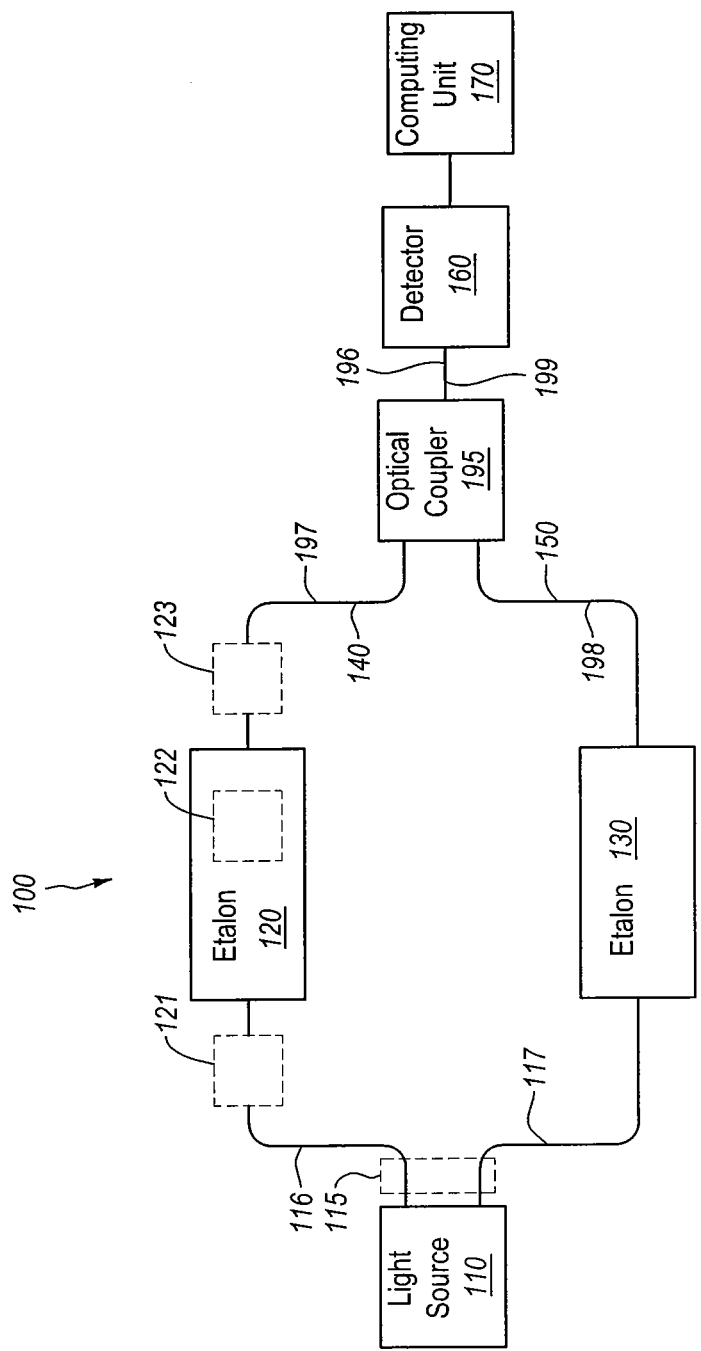
FIG. 1D illustrates another embodiment of a dual-etalon cavity-ring-down frequency-comb spectrometer system.

FIG. 1D illustrates a further embodiment of the dual-etalon cavity-ring-down frequency-comb spectrometer system 100. The embodiment of FIG. 1D includes many of the same elements of the embodiment of FIG. 1A and such repeated elements will not be explained in relation to FIG. 1D. Although not illustrated, it will be appreciated that the embodiment of FIG. 1D may include the optical filter 105 previously described. In addition, the dashed box labeled 115 illustrates that the embodiment of FIG. 1D may optionally include beam splitter 115 that generated light beam portions 116 and 117. As illustrated, the dual-etalon cavity-ring-down frequency-comb spectrometer system 100 may include an optical coupler 195, which may be any reasonable optical coupler. A first optical fiber 197 may have a first end connected to the output of the first etalon 120 and a second end connected to the optical coupler 195. A second optical fiber 198 may have a first end connected to the output of the second etalon 130 and a second end connected to the optical coupler 195. A third optical fiber 199 may have a first end connected to the optical coupler 195 and a second end connected to the detector 160. In some embodiments, the first, second, and third optical fibers, or any combination thereof, may be single mode fibers, although other mode fibers may also be used.

The optical coupler 195 may receive the first and second frequency-comb signals 140 and 150 from the first and second optical fibers 197 and 198 respectively. The optical coupler 195 may then combine the first and second frequency-comb signals 140 and 150 into a combined frequency-comb signal 196, which includes the beat frequencies previously described. The third optical fiber 199 may provide the combined frequency-comb signal 196 to the detector 160 for detection of the beat frequencies. In some embodiments, prior to providing the combined frequency-comb signal 196 to the detector 160, the optical coupler 195 may provide filtering of the combined frequency-comb signal 196 so that unwanted signal components are not provided to the detector 160.

Figure 6B:
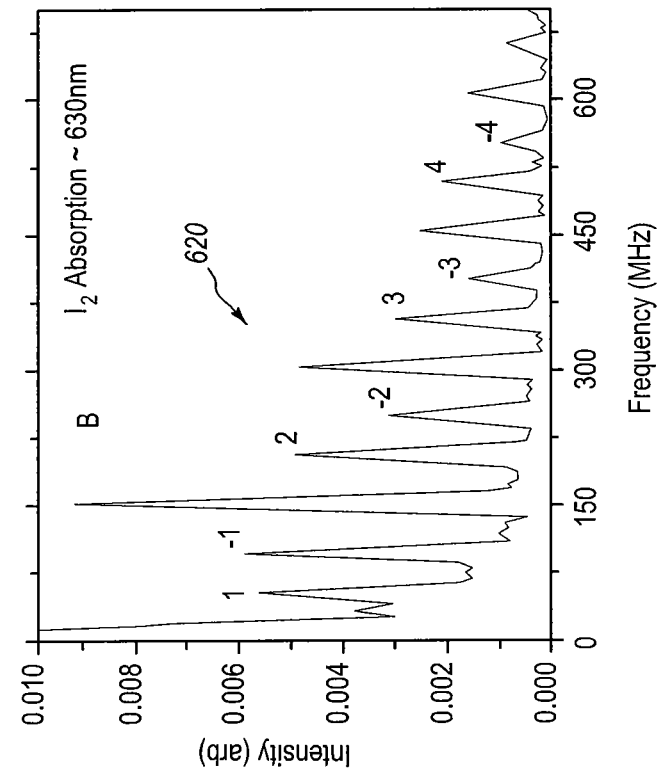
FIGS. 6A-6C illustrate an absorption measurement.
Figure 6A:
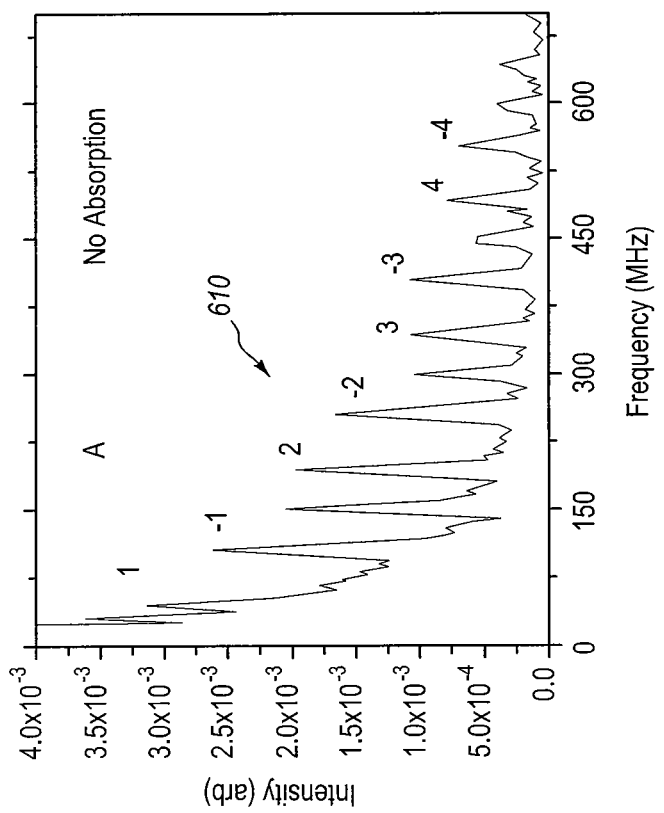
Figure 6C:
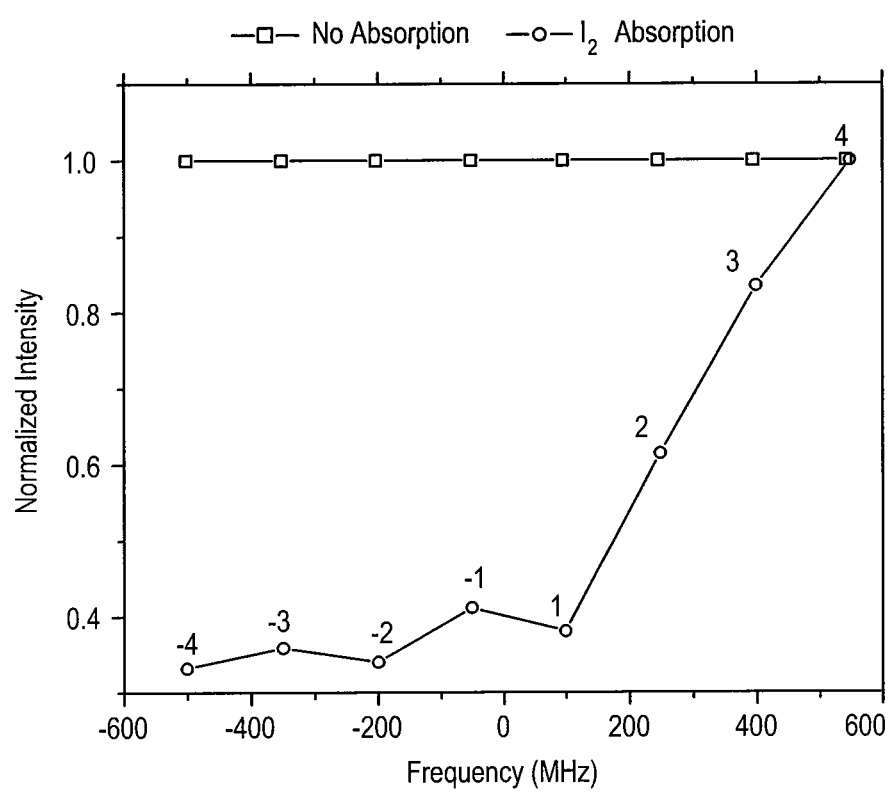

Example Operation of a Dual-Etalon Cavity-Ring-Down Frequency-Comb Spectrometer System Specific examples of the operation of an embodiment of dual-etalon cavity-ring-down frequency-comb spectroscopy will now be described with reference to the embodiment previously discussed in relation to FIG. 1D. FIGS. 2A-2C, 3A-3D, 4A-4B, and 5A-5C describe the generation of beat frequencies in the dual-etalon cavity-ring-down frequency-comb spectrometer 100 without a sample. FIGS. 6A-6C describe an absorption measurement operation using the dual-etalon cavity-ring-down frequency-comb spectrometer 100.

A single laser pulse is generated by the broad band light source 110 and split into two pulses 116 and 117 by beam splitter 115. The pulse 116 travels down an absorption arm of the spectrometer system 100. The absorption arm contains a confocal etalon 120 with a free spectral range of 150 MHz. As previously discussed, a sample may be placed inside, before, or after the etalon 120. The second pulse 117 travels down the second arm of the spectrometer system 100, the read-out arm. In the present embodiment, the read-out arm contains a short (about 1 cm in length) confocal etalon 130 with a free spectral range of 1.5 GHz.

The frequency-comb signals 140 and 150 of the two arms are each independently focused into two, single-mode fiber optic cables 197 and 198 respectively. The outputs 140 and 150 are combined into a third fiber optic 199 by the optical coupler 195 and this combined frequency-comb beam 196 illuminates a 3 GHz silicon photodiode, which is an example of the detector 160. The signal from the detector 160 is recorded on a Tektronics oscilloscope (5 GPS), which is an example of a computing unit 170, capable of performing a Fourier transform on the recorded signal. As the laser pulse used as a light source for the present embodiment has a bandwidth of approximately 1.5 GHz, approximately 10 frequencies will be transmitted through the 150 MHz absorption arm confocal etalon 120 and only a single frequency will be transmitted through the 1.5 GHz read-out arm confocal etalon 130. The resolution associated with each frequency is determined by the mirror reflectivity (ring down time) of each etalon.

When the frequency-comb signals 140 and 150 from the two arms of the spectrometer 100 are combined on the photodiode, a new set of frequencies appear in the Fourier transform of the interference pattern. The new frequencies are the beat frequencies caused by the heterodyning of the single frequency from the etalon 130 and the multiple frequencies of the etalon 120. There is one new beat frequency for each of the ten frequencies of the frequency-comb signal 140 emanating from the 150 MHz confocal etalon 120 in the absorption arm of the spectrometer 100. The frequencies of the beat frequencies are the frequency separation between the individual frequencies carried in the first and second frequency-comb signals 140 and 150.

The optical detector 160 measures the intensity of the incident light, where with c being the speed of light, $\epsilon_o$ is the permittivity of free space, and E is the electric field of the incident light. While each individual beam has its unique time structure do to the shape of $E^2$, when both arms are incident on the detector the combined intensity pattern is given by:

$$I(x,t) = c\epsilon_0 <E_1+E_2>^2/2. \quad (1)$$

This squaring of the total electric field reveals a cross term dependant on both $E_1$ and $E_2$, see equation 2 below:

$$I(x,t) = E_1^2 + E_2^2 + 2(I_1 I_2)^{1/2} \cos[\omega 1 - \omega 2)(x/(2\pi c)-t)], \quad (2)$$

where $\omega$ is the frequency of the light. From this equation we can calculate the time varying signal associated with any two interfering light fields with frequencies $\omega 1$ and $\omega 2$. The interferogram is the sum over all possible interfering pairs of light fields with no cavity ringdown. The intensity profile for a ring down cavity with and absorption is:

$$I(t) = I_0 e^{(-t/\tau - \alpha L c)} \quad (3)$$

where $\tau$ is the 1/e ringdown time of the empty cavity which is determined by the cavity mirrors and dispersion, $\alpha$ is the absorbance of the sample, and L is the length of the cavity. In general, the intensity profile for a ringdown as observed on a photo-detector (x=0) is given by;

$$I_x, t = E_1^2 e^{(-t/\tau_1 - \alpha_1 L_1 c)} + E_2^2 e^{(-t/\tau_2 - \alpha_2 L_2 c)} + \sum_{i=1}^{imax} \sqrt{I_1 I_2} \cos[(\omega_{2i} - \omega_{1i})t] e^{(\frac{-t}{2}(\frac{1}{\tau 1} + \frac{1}{\tau 2}) + \frac{c}{2}(\alpha_1 L_1 + \alpha_2 L_2))}$$

where the summation over the cross term accounts for all possible frequency pairs such that imax is determined by the bandwidth of the laser.

Figure 2A:
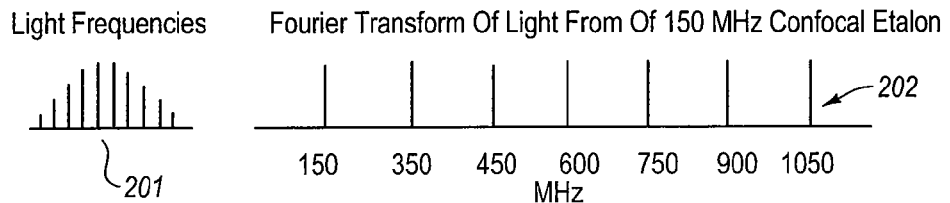
FIGS. 2A-2C illustrate expected frequency spectrums for a first frequency-comb signal, a second frequency-comb signal, and a combined frequency-comb signal.
Figure 2B:
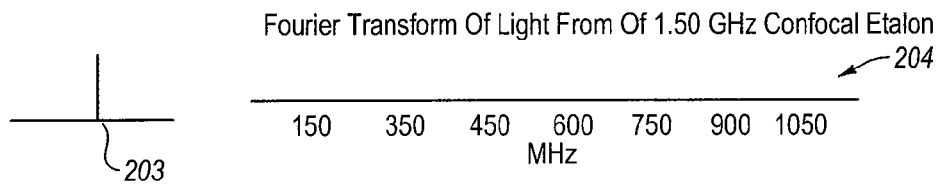

FIGS. 2A and 2B show a schematic of the expected frequencies that comprise the frequency-comb signal 140 and the frequency-comb signal 150 after the two signals exit the confocal etalons 120 and 130 respectively and the frequency interference pattern that is expected if there is no absorbing media in the etalon 120 that would absorb a specific comb tooth. For example, FIG. 2A shows an expected interference pattern 201 for the frequency-comb signal 140 with frequencies separated by the 150 MHz free spectral range of the confocal etalon 120. The Fourier transform of the expected interference pattern 201 shows a frequency spectrum 202 with frequencies at every 150 MHz from 150 MHz to 1050 MHz. FIG. 2B shows an expected interference pattern 203 for frequency-comb signal 150. The Fourier transform of the expected interference pattern 203 shows a frequency spectrum 204.

Figure 2C:
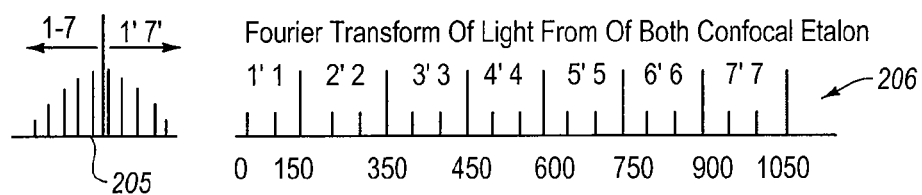

FIG. 2C shows the expected interference pattern 205 when the frequency-comb signals of FIGS. 2A and 2B are combined. The Fourier transform of the expected interference pattern 205 shows a frequency spectrum 206. As shown in FIG. 2C, the frequency spectrum 206 includes beat frequencies 1' and 1 between 0 and 150 MHz, beat frequencies 2' and 2 between 150 MHz and 300 MHz, beat frequencies 3' and 3 between 300 MHz and 450 MHz, beat frequencies 4' and 4 between 450 MHz and 600 MHz, beat frequencies 5' and 5 between 600 MHz and 750 MHz, beat frequencies 6' and 6 between 750 MHz and 900 MHz, and beat frequencies 7' and 7 between 900 MHz and 1050 MHz.

Figure 3D:
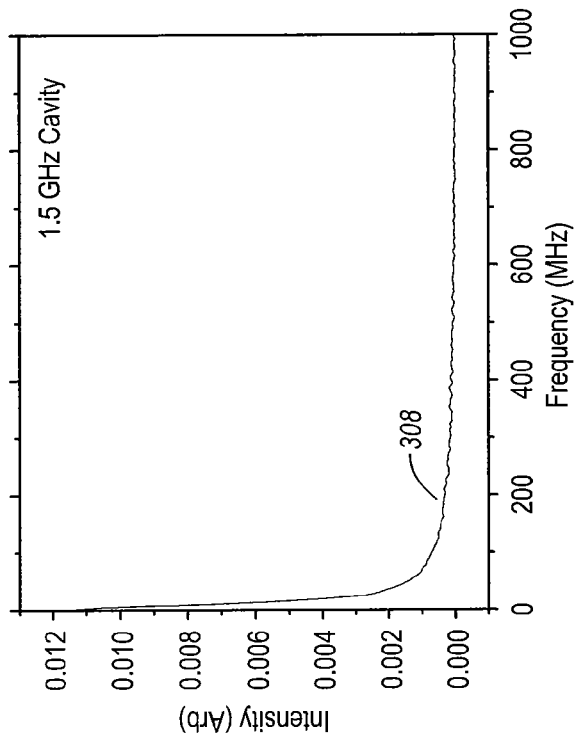

FIGS. 3A-3D illustrate measured outputs from each arm of the spectrometer 100. For example, FIG. 3A illustrates an intensity vs. time plot of an interference pattern 305 achieved by blocking the etalon 130 and letting only the output of etalon 120 strike the detector 160. As shown, the intensity of the interference pattern 305 decays with time.

When Fourier transformed, the interference pattern 305 becomes the reconstituted frequency spectrum 306. FIG. 3B illustrates intensity vs. frequency for the frequency spectrum 306. The frequency spectrum 306 consists of a set of equally spaced frequencies 306a-306f that are separated by the 150 MHz free spectral range of the confocal etalon 120. That is, frequency 306a is at 150 MHz, frequency 306b is at 300 MHz, frequency 306c is at 450 MHz, frequency 306d is at 600 MHz, frequency 306e is at 750 MHz, and frequency 306f is at 900 MHz. It is also seen that the intensity of the frequency spectrum 306 decays with increasing frequency. Comparing FIG. 3B with FIG. 2A shows that the measured frequency spectrum 306 is very close to the expected frequency spectrum 202.

Figure 3C:
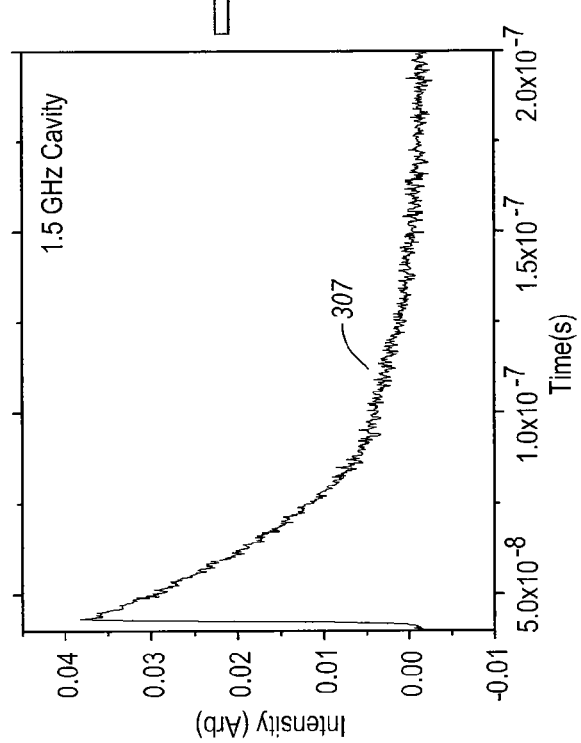

FIG. 3C illustrates an intensity vs. time plot of an interference pattern 307 achieved by blocking the etalon 120 and letting only the output of etalon 130 strike the detector 160. Since there is a single frequency existing in the etalon 130, a smooth decay over time is observed for the interference pattern 307.

When Fourier transformed, the interference pattern 307 becomes the reconstituted frequency spectrum 308. FIG. 3D illustrates intensity vs. frequency for the frequency spectrum 308. Since there is only the one frequency, no heterodyne beat frequencies are observed in the frequency spectrum 308. Comparing FIG. 3D with FIG. 2B shows that the measured frequency spectrum 308 is very close to the expected frequency spectrum 204.

Figure 4B:
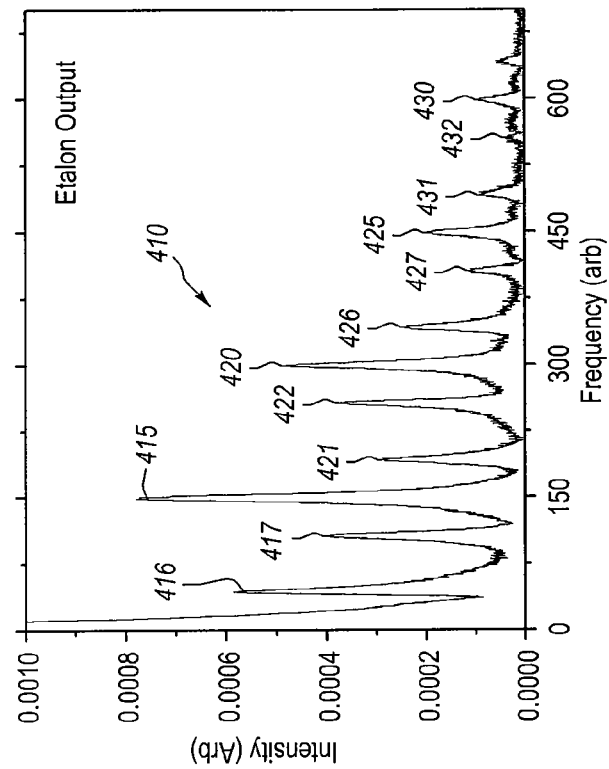
FIGS. 4A and 4B illustrate a measured interference pattern and frequency spectrum for a combined frequency-comb signal.
Figure 4A:
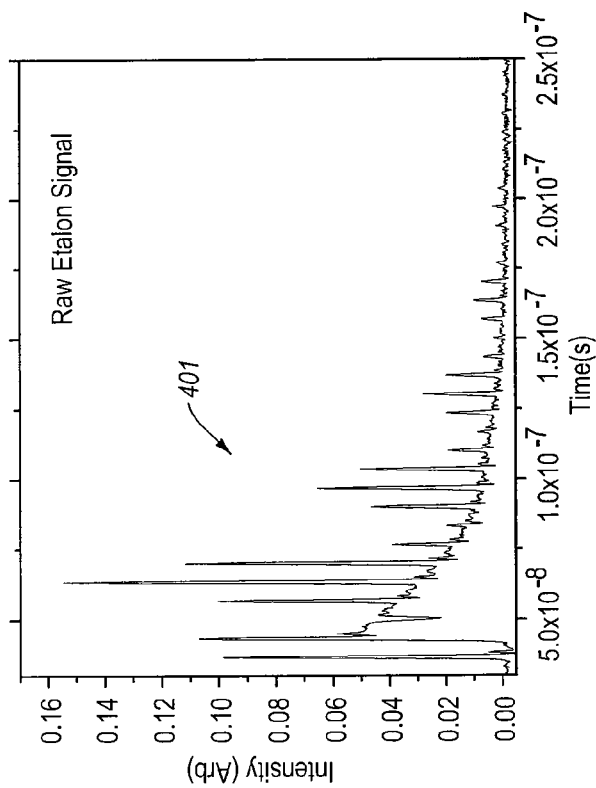

FIG. 4A shows the measured interference pattern 401 on the photodiode 160 when the first and second frequency-comb signals 140 and 150 are combined. Clear modulation in the interference pattern 401 is observed when comparing the interference pattern 401 with the interference pattern 305 of FIG. 3A.

When Fourier transformed, the interference pattern 401 becomes the reconstituted frequency spectrum 410. As shown in FIG. 4B, the frequency spectrum 410 includes a frequency 415 at 150 MHZ, a frequency 420 at 300 MHz, a frequency 425 at 450 MHz, and a frequency 430 at 600 MHz. In addition, two new beat frequencies 416 and 417 are between 0 and 150 MHz, two new beat frequencies 421 and 422 are between 150 MHz and 300 MHz, two new beat frequencies 426 and 427 are between 300 MHz and 450 MHz, and two new beat frequencies 431 and 432 are between 450 MHz and 600 MHz. The new beat frequencies of frequency spectrum 410 comport with those shown in expected frequency spectrum 206 of FIG. 2C.

Another specific example of the operation of an embodiment of dual-etalon cavity-ring-down frequency-comb spectroscopy will now be described with reference to the embodiments previously discussed in relation to FIGS. 1A-1D. This embodiment is able to provide high-resolution spectra over many thousands of GHz simultaneously.

A single laser pulse is generated by the broad band light source 110 and split into two pulses 116 and 117 by beam splitter 115. The pulse 116 travels down an absorption arm of the spectrometer system 100. The absorption arm contains a confocal etalon 120 with a free spectral range of 150 MHz. As previously discussed, a sample may be placed inside, before, or after the etalon 120. The second pulse 117 travels down the second arm of the spectrometer system 100, the read-out arm. In the present embodiment, the read-out arm contains a confocal etalon 130 that has nearly the same free spectral range of the confocol etalon 120. For example, the free spectral range of the confocol etalon 130 may be only 100 KHz different from the free spectral range of the confocol etalon 120. By making the free spectral range only 100 KHz different in frequency, then the interference pattern between the output of the two etalons 120 and 130 will be a series of beat frequencies separated by approximately 100 KHz. The number of such separated frequencies will be equal to the number of frequency-comb teeth coming from the two etalons 120 and 130. To obtain a 100 KHz separation between the two etalons, in one embodiment the etalons 120 and 130 may be approximately 10 microns different in length between the etalons 120 and 130.

FIG. 5A shows the expected interference pattern 501 and Fourier transformed frequency spectrum 502 for the frequency-comb signal 140 in this embodiment. It is noted that a frequency is found every 150 MHz.

FIG. 5B shows the expected interference pattern 503 and Fourier transformed frequency spectrum 504 for the frequency-comb signal 150 in this embodiment. It is noted that a frequency is found at approximately every 150 MHz, since there is the 100 KHz difference in free spectral range previously described.

FIG. 5C shows the expected interference pattern 505 and Fourier transformed frequency spectrum 506 that will be observed when the output of the two etalons 120 and 130 are combined on a fast photodiode. Note that the series of beat frequencies shown in frequency spectrum 506 (separated by 100 KHz in this embodiment) are repeated twice every 150 MHz. This is because there are beat frequencies not only between the nearest frequencies but between all frequencies that are present in each beam. In this manner the absorption frequency spectrum over the entire bandwidth of the light source 110 may be determined and the entire spectrum resides between 0 and 150 MHz, between 150 MHz and 300 MHz, between 300 MHz and 450 MHz, between 450 MHz and 600 MHz, between 600 MHz and 750 MHz, between 750 MHz and 900 MHz, and between 900 MHz and 1050 MHz.

Having described how the dual-etalon cavity-ring-down frequency-comb spectrometer system 100 is able to generate two frequency-comb signals using the etalons 120 and 130 and having described how a frequency spectrum of a combined frequency-comb signal is produced, an absorption measurement using the dual-etalon cavity-ring-down frequency-comb spectrometer system 100 will now be described. FIG. 6A shows a frequency spectrum 610 of a combined frequency-comb signal measured without including an absorption sample. The frequency spectrum may be produced as previously described. As illustrated in FIG. 6A, the frequency spectrum 610 includes various beat frequencies 1, −1, 2, −2, 3, −3, and 4, −4.

A sample, which in this embodiment is Iodine gas, may then be placed before, inside, or after the etalon 120 and a frequency spectrum may be produced as described above. FIG. 6B illustrates a frequency spectrum 620 of a combined frequency-comb signal measured while placing the Iodine gas sample before the etalon 120. As illustrated in FIG. 6B, the frequency spectrum 620 also includes various beat frequencies 1, −1, 2, −2, 3, −3, and 4, −4. However, a comparison of the beat frequencies in frequency spectrum 610 with those in frequency spectrum 620 shows that some of the beat frequencies are diminished, thus showing that absorption occurred at those frequencies.

To further show this, the frequency spectrum 610 obtained without a sample is used to normalize the frequency spectrum 620 obtained with the Iodine gas sample. FIG. 6C plots the normalized intensity of the individual beat frequencies from FIG. 6B normalized by the intensity of the beat frequencies of FIG. 6A. As can be seen, the falling edge of the absorption line is observed. In addition, FIG. 6C shows that beat frequencies 1, −1, −2, −3, and −4 have been extinguished between 60 and 80 percent. Accordingly, absorption of some of the light beam from light source 110 has taken place at these beat frequencies. Although in the described example the identity of the Iodine gas sample was known, an unknown sample's identity may also be determined by analyzing which light frequencies are absorbed by the dual-etalon cavity-ring-down frequency-comb spectrometer system 100. Alternatively, knowing the gas identity and the path length of the absorption cell (or ring down time of the etalon cavity) allows one to determine the concentration of the gas in the absorption cell.

In the example just described, the absorption is observed by comparing the signals with and without gas in an absorption cell placed before etalon 120. An alternative approach is to use a third etalon that is substantially identical to etalon 120 to measure the absorption light path with no gas sample and to combine the output of this identical third etalon with the output of etalon 130 to obtain a background signal at the same time as obtaining the absorption signal utilizing etalons 120 and 130 as previously described.

Figure 8A:
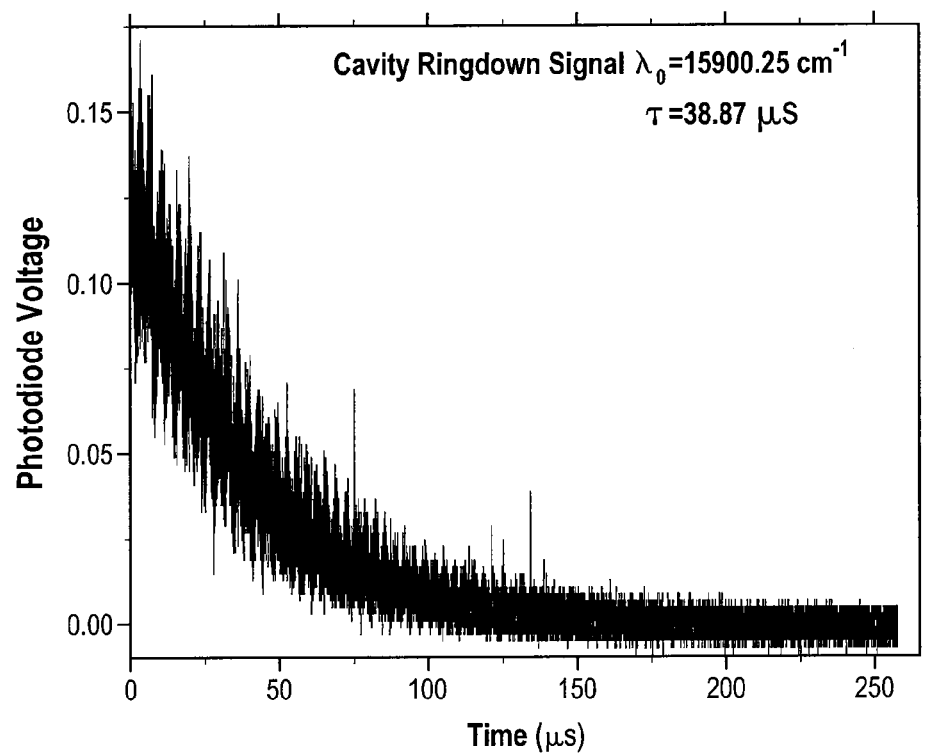
FIGS. 8A-8D illustrate further measurement aspects of the dual-etalon cavity-ring-down frequency-comb spectrometer system.
Figure 8B:
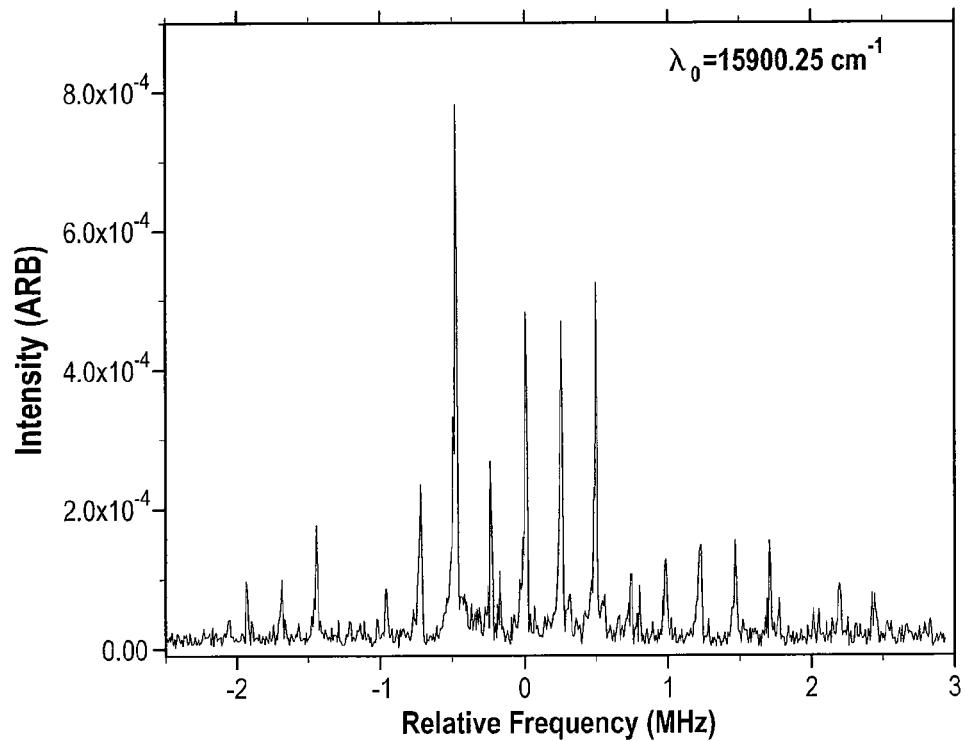
Figure 8C:
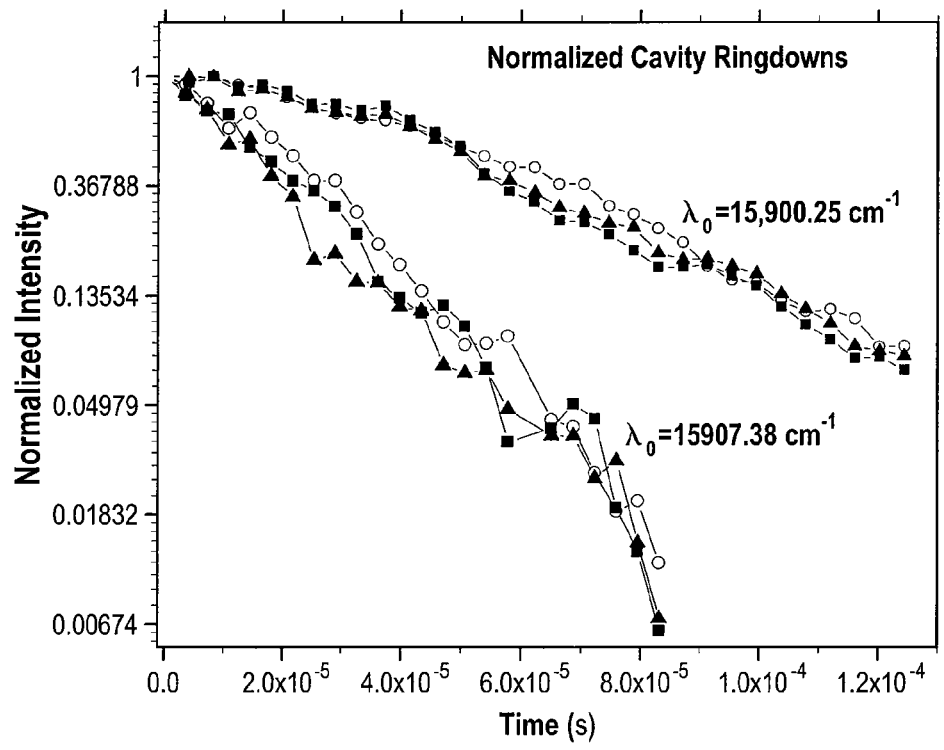
Figure 8D:
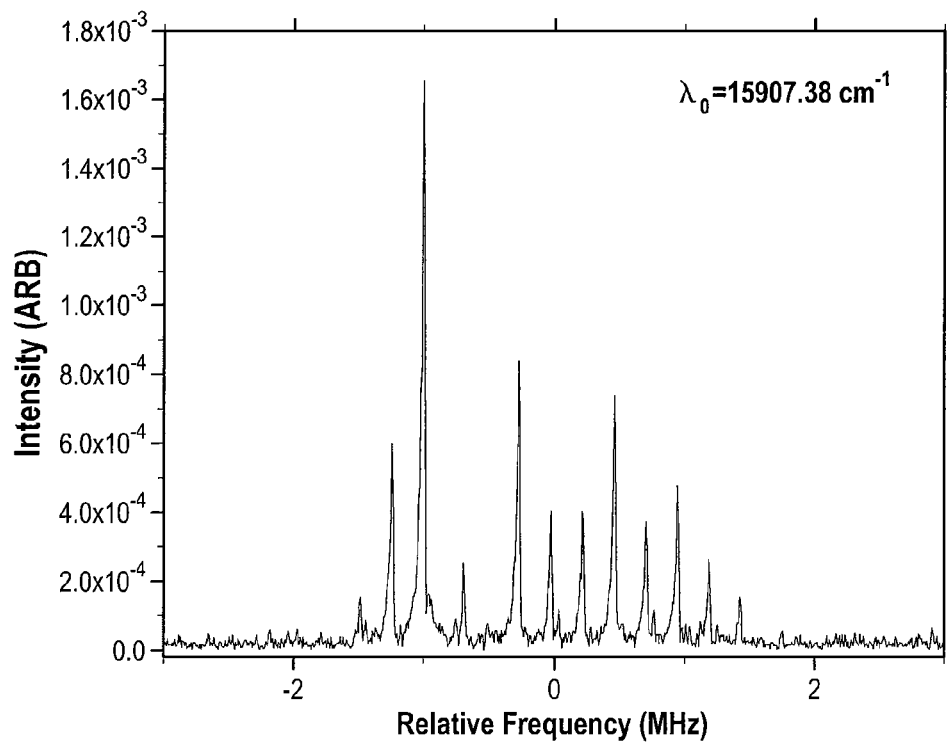

To further demonstrate how the dual-etalon cavity-ring-down frequency-comb spectrometer system 100 may perform cavity ring down spectroscopy at many wavelengths substantially simultaneously, the sample etalon 120 and the read-out etalon 130, may be filled with room pressure air. The etalon 120 may be made to operate at 300 MHz and the etalon 130 may be made to operate at 300.24 MHz. Multimode light from a Nd:YAG pumped dye laser operating near 628 nm wavelength with a bandwidth of 5 GHz may be used as the light source 110. This light is resonant with a weak absorption transition of oxygen in the air. FIG. 8A shows the time versus intensity plot from the combined outputs of frequency-comb signals 140 and 150, of the two etalons 120 and 130. FIGS. 8B and 8D are Fourier Transforms of 10 microsecond segments of the intensity versus time signal, an example of which is shown in FIG. 8A. In FIGS. 8B and 8D, is shown the cross frequency signals from the two etalons 120 and 130 at a particular 10 microsecond time slice in the decay. The frequency spectrum of FIG. 8B is taken at 15900.25 cm$^{-1}$ and is not on the oxygen resonance. The frequency spectrum of FIG. 8D is taken at 15906.38 cm$^{-1}$ and is on an oxygen resonance. In FIG. 8C is shown a plot of the logarithm of the intensity of the individual frequencies observed in FIGS. 8B and 8D as a function of time. The slope of these lines may be analyzed to determine the absorption of that particular frequency by the gas in the etalons 120 and 130. It is easy to observe by inspection of FIG. 8C that the decay of the light intensity with time when the laser is resonant with 15900.25 cm$^{-1}$ is slower (shallower slope to lines) than when the laser is resonant with the oxygen absorption at 15907.38 cm$^{-1}$ (steeper slope to lines). As the slope does not depend upon the amount of light that is initially present at a particular frequency in the etalons 120 or 130, the multi-mode nature of the light source does not influence the measurement of the gas absorption. This capability enables utilizing many different light sources for the dual-etalon cavity-ring-down frequency-comb spectrometer system 100.

Time Resolved Fourier Transform Spectroscopy

In one embodiment of the dual-etalon cavity-ring-down frequency-comb spectrometer system 100, although the broad-band light source 110 may be on for only a short period of time, for example 100 femtoseconds, the resulting interference pattern will last as long as the cavity ring down time of the etalons 120 and 130. The short pulse of light after entering the etalons 120 and 130 remain in the cavities until the light slowly leaks out. This occurs as each bounce of the light from the mirror lets a small amount of the light out of the etalon cavities. With high reflective mirrors this process can take up to 100 microseconds. After the interference pattern is recorded in the computing unit 170, a Fourier transform of each small length of the interference pattern may be performed individually, for example each 50 nanosecond length may be individually Fourier transformed. In this way, a "movie" of the absorption with 50 nanosecond resolution over the entire 100 microseconds is obtained. Each individual frame of the movie would contain the entire absorption frequency spectrum with approximately 150 MHz frequency resolution (the free spectral range of etalon 120, in this example 150 MHz). The entire time spectrum would be recorded every 50 nanoseconds for the entire 100 microseconds of the ring-down time of the etalons. As the Fourier transform of 50 nanoseconds is 20 MHz and if the Free Spectral Range of the two etalons 120 and 130 are more than 20 MHz separated, then each frequency emitted by etalon 120 can be resolved in each 50 nanosecond piece of the interferogram. In this manner a high frequency resolution, multi-spectral movie having 50 nanoseconds time resolution of the sample can be achieved. The desired frequency resolution, frequency bandwidth and time resolution are all parameters that can be changed by adjustments to the etalons 120 and 130 and by adjusting the light source 110.

To obtain equivalent spectral resolution (150 MHz) with a traditional Fourier transform spectrometer utilizing a moving mirror would require a mirror travel of fifty feet. In order to obtain the time resolution, one typically performs a step scan of the mirror. That is, the time changing absorption must be a reproducible event, like a photolysis of a molecule, to produce a radical whose changing absorption spectra one desired to record. In this case, a photolysis pulse would cause the radical to be formed and the interference pattern would be recorded at a set mirror position. Then, the mirror is moved and the photolysis is repeated. This would be done until the desired resolution is obtained. This can take many hours.

Comparable information may be obtained with the embodiments disclosed herein following a single photolysis pulse. If better signal to noise ratio is needed, then several interference patterns from successive photolysis pulses may be averaged together. The embodiments disclosed herein here are six or seven orders of magnitude faster than traditional time-resolved Fourier transform spectroscopy and over an order of magnitude higher in resolution than traditional Fourier Transform spectroscopies.

In another embodiment of the spectrometer 100 shown in FIG. 1C, the combined frequency-comb signal 191 of the etalons 120 and 130 may be passed through a sample containing a gas that after absorption of the light fluoresces and that fluorescence can be monitored. If in the sample a particular molecule or atom is simultaneously resonant with more than one frequency of light that is present in the combined frequency-comb signal 191 and that molecule has a short fluorescent lifetime relative to the beat frequency between any two light frequencies that it can absorb, then that gas molecule will reflect the beat frequency in its fluorescence and broad-band, high resolution laser induced fluorescence measurements can be made in this manner.

Other Applications

In one embodiment, the dual-etalon cavity-ring-down frequency-comb spectrometer system 100 may be used for distance displacement measurements. In such embodiments, the beat frequencies that are measured are a sensitive measure of the difference in length of the two etalons 120 and 130. If one of the etalons is held constant and the other is changed, the beat frequencies will shift. Assuming that the light source 110 is operating at 600 nm (red), then if the length of one of the etalons changes by 600 nm the beat frequency pattern will span an entire free-spectral range of the etalon. Assuming the free spectral range of the etalon is 300 MHz (half meter long etalon with light beam down the middle of the cavity), then 600 nm in path length change is reflected in a 300 MHz in frequency shift of the beat frequency. As the beat frequency may be measured to approximately 10 KHz in some embodiments, (when the lifetime of the cavity is ~100 Microseconds) then the path length change of 10 KHz/300,000 KHz*600 nm=$2*10^{-11}$ meters or 20 picometers of length change of the etalon cavities may be measured. This results in a high accuracy for a distance displacement measurement.

In one embodiment, the dual-etalon cavity-ring-down frequency-comb spectrometer system 100 may be used for a communication application. In such embodiment, if the light source 110 output is passed through an apparatus or medium that eliminates a pattern of optical frequencies before the light beam enters the etalon 120 and the etalon 130, then the beat pattern which is observed will change correspondingly. In one embodiment, the light beam from the light source 110 is dispersed and then placed through a multi-element mask that either transmitted or reflected certain colors of light, thereby imprinting information onto the light frequencies. The individual light frequencies would be recombined into a single light beam by passing through a second dispersive medium.

This light beam with certain frequencies present and certain frequencies eliminated would then be put into the etalon 120 and the etalon 130. The etalon 120 and the etalon 130 would create two frequency-comb signals 140 and 150 that would have an interference pattern that reflected the light that was put through the multi-element mask, each with a small difference in spacing. By transmitting this single pulse of light (the combined output of the etalon 120 and the etalon 130) and Fourier transforming the received pulse, one could reconstruct the original frequency spectrum that was imposed upon the light pulse.

This detection scheme would only require a single photon detector to record the interference pattern. Technology exists to impose 1000 element mask and therefore, generate, transmit and recover 1000 equally spaced frequencies whose entire transmission pulse lasted approximately 10 microseconds. The number of possible combination of on and off frequencies in a single laser pulse would then be $2^{1000}$ or approximately $10^{103}$ possible combination that may be transmitted in a single 10 microsecond long pulse.

Example Methods

Figure 7:
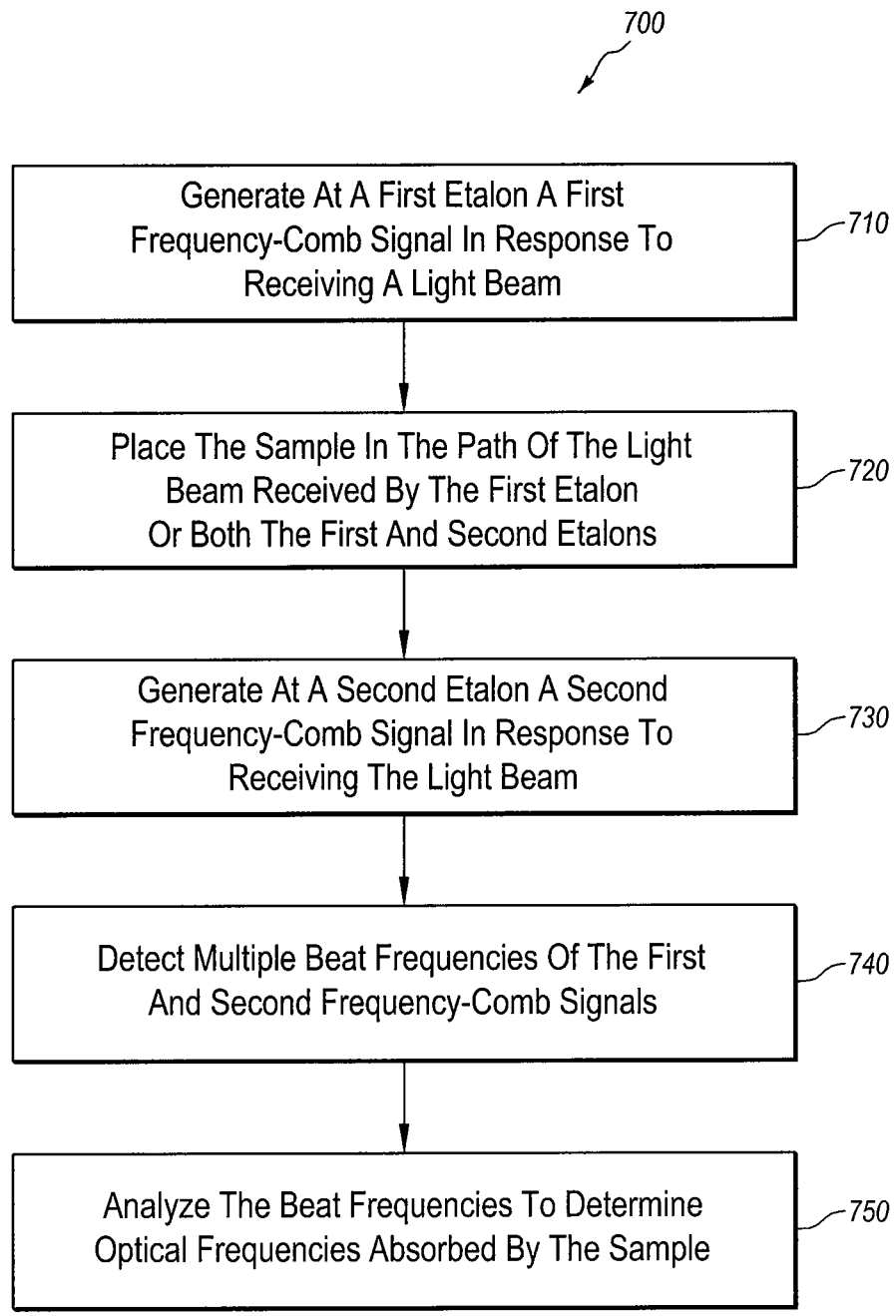
FIG. 7 illustrates a flow chart of a method for performing frequency-comb spectroscopy on a sample according to an embodiment.

FIG. 7 is a flow diagram of an illustrative embodiment of a method 700 for performing frequency-comb spectroscopy on a sample. In the illustrated embodiment, the method 700, and other methods and processes described herein, set forth various functional blocks or actions that may be described as processing steps, functional operations, events and/or acts, etc., which may be performed by hardware, software, and/or firmware. The method 700 includes one or more operations as illustrated by acts 710, 720, 730, 740 and 750.

The method 700 includes an act 710 of generating at a first etalon a first frequency-comb signal in response to receiving a light beam, the first frequency-comb signal defining a spectrum of light that includes multiple optical frequencies spaced by a first frequency spacing. For example, as previously described the first etalon 120 generates the first frequency-comb signal 140 in response to receiving a light beam from the broad band light source 110. The first frequency-comb signal 140 includes the first spacing that is at least partially determined by the FSR of the first etalon 120.

The method 700 includes an act 720 of placing the sample before, inside, or outside of one or more of the first etalon and the second etalon such that the sample is in the path of the light beam received by the first etalon or both the first and second etalons. For example, as previously discussed the sample may be placed before the first etalon 120 as shown at 121, inside the first etalon 120 as shown at 122, or after the first etalon as shown at 123. When the sample is placed inside the first etalon 120, a cavity-ring-down arrangement is obtained. As also explained, in some embodiments the sample may be placed before, after, or inside of both the first and second etalons 120 and 130.

The method 700 further includes an act 730 of generating at a second etalon a second frequency-comb signal in response to receiving the light beam from the at least one broad band light source, the second frequency-comb signal defining a second spectrum of light that includes one or more optical frequencies spaced by a second frequency spacing that is different from the first frequency spacing. For example, as previously described the second etalon 130 generates the second frequency-comb signal 150 in response to receiving the light beam from the broad band light source 110. The second frequency-comb signal 150 includes the second spacing that is at least partially determined by the FSR of the second etalon 130 and is different from the first spacing of the first frequency-comb signal 140.

The method 700 also includes an act 740 of detecting multiple beat frequencies of the first and second frequency-comb signals. For example, as previously described the detector 160 combines the first and second frequency-comb signals and then detects beat frequencies caused by the difference in the first and second spacings.

The method 700 includes an act 750 of analyzing the beat frequencies to determine optical frequencies absorbed by the sample. For example, the computing unit 170 may record an interference pattern obtained from the beat frequencies. The computing unit 170 may reconstitute an absorption frequency spectrum of the beat frequencies by performing a Fourier Transform operation on the interference pattern; and based on the reconstituted absorption frequency spectrum, may determine which of the beat frequencies was at least partially absorbed by the sample. In some embodiments, a comparison of the reconstituted absorption frequency spectrum with a frequency spectrum reconstituted from an interference pattern obtained from beat frequencies of the first frequency-comb signal and the second frequency-comb signal obtained without the sample may be done to determine where absorption occurred.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Embodiments of the invention include or are incorporated in computer-readable storage media having computer-executable instructions or data structures stored thereon. Examples of computer-readable storage media include RAM, ROM, EEPROM, CD-ROM, or other optical disk storage, magnetic disk storage or other magnetic storage devices, or any other medium capable of storing instructions of data structures and capable of being accessed by portable electronics devices (e.g., personal audio players), general purpose or special purpose computers, personal digital assistants, mobile telephones, and other devices with data processing capabilities. Computer-readable media also encompasses combinations of the foregoing structures. Computer-executable instructions comprise, for example, instructions and data that cause general purpose computers, special purpose computers, or other processing devices, such as personal digital assistants or mobile telephones, to execute a certain function or group of functions. The computer-executable instructions and associated data structures represent an example of program code means for executing the steps of the invention disclosed herein. Examples of computer-executable instructions include those used to perform the method 700 described in relation to FIG. 7.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for performing frequency-comb measurements, comprising:
   at least one broad band light source configured to provide a light beam;
   a first etalon configured to generate a first frequency-comb signal in response to receiving the light beam from the at least one broad band light source, the first frequency-comb signal defining a spectrum of light that includes multiple optical frequencies spaced by a first frequency spacing;
   a second etalon configured to generate a second frequency-comb signal in response to receiving the light beam from the at least one broad band light source, the second frequency-comb signal defining a second spectrum of light that includes one or more optical frequencies spaced by a second frequency spacing that is different from the first frequency spacing; and
   a detector configured to detect multiple beat frequencies of the first and second frequency-comb signals.

2. The system of claim 1, further comprising at least one computing unit configured to analyze the beat frequencies to determine optical frequencies absorbed by a sample.

3. The system of claim 2, wherein the at least one computing unit is configured to perform a Fourier Transform when analyzing the beat frequencies.

4. The system of claim 2, wherein the system is configured so that the sample may be placed inside or closely adjacent to the first etalon or placed inside or closely adjacent to both the first and second etalons when the sample is being tested for absorption of at least part of the light beam.

5. The system of claim 1, further comprising a beam splitter configured to:
   receive the light beam from the at least one broad band light source;
   divide the light beam into a first portion and a second portion;
   provide the first portion of the light beam to the first etalon; and
   provide the second portion of the light beam to the second etalon.

6. The system of claim 1, further comprising a beam combiner located between the first and second etalons and the detector, the beam combiner configured to:
   receive the first and second frequency comb signals;
   combine the first and second frequency-comb signals into a combined frequency-comb signal; and
   provide the combined frequency-comb signal to the detector.

7. The system of claim 1, further comprising:
   a first optical fiber having a first end connected to the output of the first etalon;
   a second optical fiber having a second end connected to the output of the second etalon;
   a optical coupler connected to a second end of the first optical fiber and a second end of the second optical fiber; and
   a third optical fiber having a first end connected to the optical coupler and a second end connected to the detector,
   wherein the optical coupler is configured to receive the first and second frequency-comb signals from the first and second optical fibers, combine the first and second frequency-comb signals into a combined frequency-comb signal, and provide the combined frequency comb signal to the third optical fiber,
   wherein the third optical fiber is configured to provide the combined frequency comb signal to the detector.

8. The system of claim 7, wherein at least one of the first, second, and third optical fibers is a single mode optical fiber.

9. The system of claim 7, wherein the optical coupler provides signal filtering of the combined frequency comb signal.

10. The system of claim 1, wherein the at least one broad band light source is a Fourier transformed limited light pulse.

11. The system of claim 1, wherein the at least one broad band light source is a non-frequency-comb laser.

12. The system of claim 1, wherein the at least one broad band light source is one of a pulsed laser, a continuous laser, a light emitting diode, or a lamp.

13. The system of claim 1, wherein the free spectral range of the second etalon is substantially the same as the free spectral range of the first etalon.

14. The system of claim 1, wherein the frequency-comb measurements comprise a distance displacement measurement.

15. The system of claim 1, wherein the frequency-comb measurements comprise a communication application measurement.

16. A method for performing frequency-comb spectroscopy on a sample, comprising:
   generating at a first etalon a first frequency-comb signal in response to receiving a light beam, the first frequency-comb signal defining a spectrum of light that includes multiple optical frequencies spaced by a first frequency spacing;

placing the sample before, inside, or outside of one or more of the first etalon or the second etalon such that the sample is in the path of the light beam received by the first etalon or both the first and second etalons;

generating at a second etalon a second frequency-comb signal in response to receiving the light beam, the second frequency-comb signal defining a second spectrum of light that includes one or more optical frequencies spaced by a second frequency spacing that is different from the first frequency spacing;

detecting multiple beat frequencies of the first and second frequency-comb signals; and analyzing the beat frequencies to determine optical frequencies absorbed by the sample.

17. The method of claim 16, wherein analyzing the beat frequencies comprises:

recording an interference pattern obtained from the beat frequencies;

reconstituting an absorption spectrum of the beat frequencies by performing a Fourier Transform operation on the interference pattern; and based on the reconstituted absorption spectrum, determining which of the beat frequencies was at least partially absorbed by the sample.

18. The method of claim 17, wherein determining which of the beat frequencies was at least partially absorbed by the sample comprises:

comparing the reconstituted absorption spectrum with a frequency spectrum reconstituted from an interference pattern obtained from beat frequencies of the first frequency-comb signal and the second frequency-comb signal obtained without the sample.

19. The method of claim 16, further comprising:

combining the first and second frequency-comb signals into a third frequency-comb signal; and providing the third frequency-comb signal for detection of the beat frequencies.

20. A system for performing frequency-comb spectroscopy on a sample, comprising:

at least one non-frequency-comb light source configured to provide a light beam;

a beam splitter configured to split the light beam into a first light beam portion and a second light beam portion;

a first etalon configured to generate a first frequency-comb signal in response to receiving the first light beam portion from the beam splitter, the first frequency-comb signal defining a spectrum of light that includes multiple optical frequencies spaced by a first frequency spacing;

a second etalon configured to generate a second frequency-comb signal in response to receiving the second light beam portion from the beam splitter, the second frequency-comb signal defining a second spectrum of light that includes one or more optical frequencies spaced by a second frequency spacing that is different from the first frequency spacing;

a first optical fiber having a first end connected to the output of the first etalon;

a second optical fiber having a second end connected to the output of the second etalon;

an optical coupler connected to a second end of the first optical fiber and a second end of the second optical fiber; and a third optical fiber having a first end connected to the optical coupler and a second end connected to a detector, wherein the optical coupler is configured to receive the first and second frequency-comb signals from the first and second optical fibers, combine the first and second frequency-comb signals into a combined frequency-comb signal, and provide the combined frequency comb signal to the third optical fiber, wherein the third optical fiber is configured to provide the combined frequency comb signal to the detector; and the detector configured to detect multiple beat frequencies of the combined frequency-comb signal; and at least one computing unit configured to:

record an interference pattern obtained from the multiple beat frequencies of the combined frequency-comb signal;

reconstitute an absorption spectrum of the beat frequencies by performing a Fourier Transform operation on the interference pattern; and based on the reconstituted absorption spectrum, determining which of the beat frequencies was at least partially absorbed by the sample.

21. The system of claim 20, further comprising an optical filter connected to the beam splitter, the optical filter configured to filter out undesired optical modes from the first light beam portion prior to first light beam portion being provided to the first etalon and to filter out undesired optical modes from the second light beam portion prior to second light beam portion being provided to the second etalon.

* * * * *